United States Patent [19]

Austin

[11] Patent Number: 5,594,018
[45] Date of Patent: Jan. 14, 1997

[54] 2-(B-BRANCHED ALKYL)-BENZIOSOTHIAZOLIN-3-ONES

[75] Inventor: Peter W. Austin, Bury, United Kingdom

[73] Assignee: Zeneca Limited, London, England

[21] Appl. No.: 501,039

[22] PCT Filed: Feb. 17, 1994

[86] PCT No.: PCT/GB94/00320

§ 371 Date: Aug. 9, 1995

§ 102(e) Date: Aug. 9, 1995

[87] PCT Pub. No.: WO94/20479

PCT Pub. Date: Sep. 15, 1994

[30] Foreign Application Priority Data

Mar. 10, 1993 [GB] United Kingdom ............... 9304903

[51] Int. Cl.$^6$ ............... C09D 5/16; A01N 43/80; C07D 275/04
[52] U.S. Cl. ............... 514/313; 548/209; 106/18.33; 528/935; 804/269
[58] Field of Search ............... 504/269; 548/209; 514/373; 528/935; 106/18.33

[56] References Cited

U.S. PATENT DOCUMENTS 3,761,488  9/1973  Lewis et al. ............... 260/302

FOREIGN PATENT DOCUMENTS 18100   10/1980  European Pat. Off. .
475123   3/1992  European Pat. Off. .
848130   9/1960  United Kingdom .

OTHER PUBLICATIONS

Chemical Abstracts, vol. 68, No. 25, Jun. 17, 1968, abstract No. 114493,.
Ponci, R. et al: "Bis(2–carboxyphenyl) disulfide diamides and benzisothiazolinones. Influence of butyl groups on antifungal activity", Farmaco Ed. Sci., 22(12), 1967, 999–1010.
Baggaley et al., J. Med. Chem., 1985, 28, 1661–67 1985.
Ricci, et al., Phytochemistry, 29(9), 2787–91 1990.
Ambrosoli, et al., Boll. Chim. Farm., 109, 251–58 1970.
Massimo, et al., II Farmaco, 45(4), 439–46 1990.
Zani, et al., II Farmaco, 46(5), 639–46 1991.
Vitali et al., II Farmaco Ed. Sc., 23(11), 1075–80 1968.
Vitali et al., II Farmaco Ed. Sc., 23(5), 468–76 1968.
Kamigata, et al., Org. Prep. Proc. Int., 15(5), 315–19 1983.
Uchida, et al., Bull. Chem. Soc. Jpn., 55, 1183–87 1982.
Ponci et al., II Farmaco Ed. Sc., XXII(12), 999–1010 1967.
Krische et al., Chem. Ber., 116, 1708–27 1983.

*Primary Examiner*—Joseph K. McKane
*Assistant Examiner*—Laura R. Cross
*Attorney, Agent, or Firm*—Cushman Darby & Cushman IP Group Pillsbury Madison & Sutro, LLP

[57] ABSTRACT

The invention relates to N-(β-branched alkyl)-1,2-benzisothiazolin-3-ones having two or more carbon atoms in the alkyl side chain such as N-(2-ethylhexyl)-1,2-benzisothiazolin-3-one, which are suitable as paint film fungicides.

8 Claims, No Drawings

2-(B-BRANCHED ALKYL)-BENZIOSOTHIAZOLIN-3-ONES

This application is a 371 of PCT/GB94/00320 filed Feb. 17, 1994.

The present invention relates to N-(β-branched alkyl)-1,2-benziso-thiolin-3-ones, and to their preparation and their use as industrial biocides.

N-alkyl-1,2-benzisothiazolin-3-ones (hereinafter referred to as N-alkyl-BIT) constitute an important group of industrial biocides which are particularly effective in inhibiting the growth of bacteria and fungi. Compounds of this type, their preparation and use are disclosed in GB 848,130 where the N-alkyl group contains at least 4 carbon atoms, including α- branched alkyl groups such as tertiary butyl. DE 4027378 discloses N-(linear $C_{6-8}$-alkyl)- BIT which are particularly effective against fungi. U.S. Pat. No. 3,761,488 discloses N-alkyl isothiazolinones but the only disclosed N-(β-branched alkyl)isothiazolonones were reported to have inferior micro-biological activity compared with their linear alkyl analogues. Whereas the known N-alkyl-BIT's are reported to be effective against a broad spectrum of micro-organisms, industry is constantly seeking more active and cost-effective compounds. A new class of N-alkyl-BIT's has now been found with increased activity against micro-organisms, especially fungi. This is particularly surprising in the light of the reported results in U.S. Pat. No. 3,761,488.

According to the invention there is provided a compound of formula (I)

and salts thereof
wherein
R and $R^1$ are alkyl or substituted alkyl containing at least 2 carbon atoms;
$R^2$ is hydrogen, alkyl or substituted alkyl; or
R and $R^1$ together with the carbon atom to which they are attached complete a ring;
X is halogen, $C_{1-4}$-lower alkyl, $C_{1-4}$-lower alkoxy, nitro, nitrile, hydroxy, carboxy or alkoxy carbonyl; and
n is 0 to 4.

The total number of carbon atoms represented by R, $R^1$ and $R^2$ (when not hydrogen) is preferably less than 18, more preferably less than 12 and especially less than 10.

When the phenyl ring of formula I is substituted, n is preferably 1 and X is preferably located in the 6-position of the BIT ring structure. It is, however, especially preferred that the phenyl ring is unsubstituted, i.e. n is preferably 0.

When R, $R^1$ or $R^2$ is substituted alkyl, the substituent is phenyl cyclohexyl, halogen, nitro, nitrile, hydroxy, carboxy, alkoxycarbonyl, acyloxy or $C_{1-4}$-lower alkoxy. It is preferred, however, that R, $R^1$ and $R^2$ are unsubstituted, and it is especially preferred that $R^2$ is hydrogen. Preferably $R^1$ is $C_{2-4}$-alkyl and R is preferably $C_{2-10}$-alkyl and especially $C_{2-8}$-alkyl.

When R and $R^1$ together with the carbon atom to which they are attached complete a ring the ring is preferably alicyclic and is preferably a 3-, 5- or especially a 6-membered ring. In such compounds, $R^2$ is preferably hydrogen. An especially preferred ring is cyclohexyl.

When X is halogen, it is preferably fluorine, or bromine and especially chlorine.

Whilst the compound of formula I is shown in the free amine form, it is also active in the form of a salt with an acid. The acid may be inorganic or organic. Examples of such acids are hydrochloric, sulphuric, citric and tartaric acids.

N-(2-ethylhexyl)-BIT and N-(2-ethylbutyl)-BIT have been found especially useful.

The compounds of formula I may be prepared by known methods for preparing N-substituted BIT's.

(1) A first method is by reacting of a 2-halosulphenylbenzoyl halide of formula II wherein X and n are as hereinbefore defined and Hal is Halogen, especially chlorine with an amine of formula (III)

in an appropriate inert solvent wherein. R, $R^1$ and $R^2$ are as hereinbefore defined. The preparation of 2-chlorosulphenyl-benzoyl chloride is described in "Synthetic Communications, 1983, 13 (12), 977 and its reaction with amines.

(2) A second method is by reacting a 2-substituted sulphinyl benzamide of formula IV in an inert organic solvent with an acid halide wherein
$R^4$ is the group $$-NHCH_2-\underset{\underset{R^2}{|}}{\overset{\overset{R^1}{|}}{C}}-R;$$

$R^5$ is $C_{1-16}$-alky, aryl or aralkyl; and
R, $R^1$, $R^2$, X and n are as hereinbefore defined.

Preferably $R^5$ is benzyl and the acid halide is preferably thionyl chloride, phosgene or proponyl chloride. Processes of this type are described in J.C.S. Chem. Comm. 1981, 510 and EP 419075.

(3) A third method is by reacting an alkali metal salt of BIT of formula (V)

with an alkyl halide, especially an alkyl bromide of formula VI in an appropriate inert solvent wherein R, $R^1$,$R^2$, X and n are as hereinbefore defined and M is an alkali metal cation such as lithium, potassium as sodium. Such a synthesis often results in mixtures of N-alkyl and O-alkyl-BIT's and is consequently less preferred. This is described further in Example 1. (4) A fourth, and preferred, method is by reacting a dithiodibenzoyl chloride (DTDBC) of formula VII

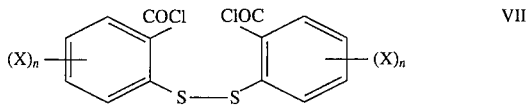

with an amine of formula III to give a $2,2^1$-dithiodi-N-(2-β-branched alkyl)-dibenzamide of formula VIII

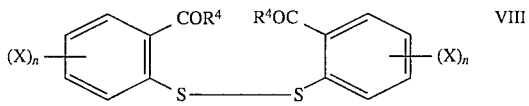

and cyclising the resulting dibenzamide in an inert organic solvent in the presence of an oxidising agent to give a compound of formula I. X, n and $R^4$ are as hereinbefore defined.

The preparation of DTDBC is described in Ber.(1926), 59, 1077 and Ber.(1928), 61, 1311; and the cyclisation of $2,2^1$-dithiobenzamides to give N-alkyl-BIT's is described in GB 848,130. It is preferred, however, that the cyclisation of the dithiobenzamide is carried out in the presence of an oxidizing agent such as chlorine, iodine, thionyl chloride, sulphuryl chloride, air or a peroxide such as hydrogen peroxide.

According to a further feature of the invention there is provided a process for the preparation of a compound of formula I by the aforementioned methods.

The compounds of formula I have antimicrobial properties and are especially active against fungi. They are especially suitable for use as industrial biocides. They exhibit good wet state preservation properties and hence may be used as preservatives for cutting fluids, cooling waters, paper mill liquors and industrially-important liquid formulations, especially aqueous-based formulations, which are used for coloration, such as liquid dyestuff formulations, aqueous-based printing inks and paints, especially latices, or for agrochemical formulations such as herbicide and pesticide flowables.

Other important applications of the compounds of formula I include their use in hydrocarbon fluids such as diesel fuels. They may also be incorporated into adhesives, cosmetics, personal care products wool and leather in order to inhibit microbial spoilage.

A preferred use of compounds of formula I is for the preservation of polyvinyl acrylate and particularly acrylic latices, especially alkaline latices of pH above 7, and more especially those containing ammonia or amines.

Compounds of formula I may be used alone for antimicrobial preservation but are preferably used in conjunction with a suitable carrier.

For ease of handling and dosing, it is generally convenient to formulate the compound of formula I as a solid, but more preferably as a liquid composition and especially a solution.

According to a further aspect of the present invention there is provided a composition comprising a carrier and a compound of formula I (hereinafter referred to as a "biocide composition").

The carrier may be a material which shows little, if any, antimicrobial activity and may be, or include, a medium which is susceptible to the growth of micro-organisms, such as bacteria or fungi. The carrier may be a solid but is preferably a liquid medium and the biocide composition is preferably a solution, suspension or emulsion of the compound of general formula I in a liquid medium.

The carrier is generally selected so that the biocide composition is compatible with the medium to be protected. Thus, for example, if the medium to be protected is a solvent-based paint, lacquer or varnish the carrier is preferably a solvent, especially a non-polar solvent such as white spirits. If the medium to be protected is a plastics material, the carrier is preferably a plasticiser typically used in the fabrication of plastic articles such as dioctylphthalate or epoxidised soya bean oil. If the medium to be protected is an aqueous medium, the carrier is preferably water or a water-miscible organic solvent or mixture thereof. Examples of suitable water-miscible organic solvents are acetic acid, N,N-dimethylformamide, propylene glycol, dipropylene glycol, methanol, ethanol, dimethylsulphoxide, N-methyl-2-pyrrolidone and lower $C_{1-4}$-alkyl carbitols such as methyl carbitol. If the carrier is a solid, the composition may be a dry solid as described in EP 407024.

If the biocide composition is in the form of a suspension or emulsion, it preferably also contains a surface active agent to produce a stable dispersion or to maintain the non-continuous phase uniformly distributed throughout the continuous phase. Any surface active agent which does not adversely affect the biocidal activity of the compound of formula I may be used, for example alkylene oxide adducts of fatty alcohols, alkyl phenols, amines such as ethylene diamine and anionic surfactants such as adducts of naphthol sulphonates and formaldehyde.

The composition may also contain one or more compounds which are capable of reacting with metals, especially iron, copper and brass. Such compounds include those well-known to the art such as metal chelants and include ethylenediamine tetra acetic acid, phenolic hydroximes such as 2-hydroxy-5-nonyl benzaldoxime and benzimidazoles and benzotriazoles especially those containing an alkyl chain. Light stabilisers and inorganic white pigments may also be present in the composition such as hydroxybenzophenones for example 2-hydroxy-, 4-hydroxy- and 2,4-dihydroxybenzophenone, hindered amines such as triacetoneamine and its derivatives, titanium dioxide, zinc oxide and calcium carbonate.

The concentration of the compound of formula I in the biocide composition is preferably up to a level at which the biocide composition is stable under the conditions of storage or transportation and is preferably from 1 to 50%, especially from 5 to 30% and more especially from 10 to 20% by weight relative to the total weight of the biocide composition.

The compounds of general formula I or compositions containing a compound of formula I can be used for the treatment of various media to inhibit the growth of micro-organisms and are especially effective in providing antifungal activity.

As a further aspect of the present invention there is provided a method for inhibiting the growth of micro-organisms on, or in, a medium which comprises treating the medium with a compound of formula I or the biocide composition.

The compound of formula I can be used in conditions in which micro-organisms grow and cause problems. Systems in which micro-organisms cause problems include liquid, particularly aqueous, systems such as cooling water liquors, paper mill liquors, metal working fluids, geological drilling lubricants, polymer emulsions and especially surface coating compositions such as latex, paints, varnishes and lacquers and also solid materials such as wood, plastics materials and leather. The compound of formula I can be included in such materials to provide an anti-microbial effect. The amount of the compound is typically in the range from 0.0001 to 2.0% preferably from 0.001 to 1% and especially from 0.002 to 0.5% by weight of the compound relative to the system to which it is added. In certain cases, microbial inhibition has been obtained with from 0.0005% to 0.01% by weight of the compound of formula I.

The compound of formula I may be the only antimicrobial compound used to protect the medium or it may be used together with one or more different compounds of formula I or with one or more other compounds having antimicrobial activity. A mixture of anti-microbial compounds hereinafter referred to as a "biocide mixture" often has a broader anti-microbial spectrum and hence is more generally effective than the components of the mixture. The other antimicrobial compound or compounds may possess anti-bacterial, anti-fungal, anti-algal or other antimicrobial activity. The biocide mixture typically contains from 1 to 99% by weight, and preferably from 40 to 60% by weight, of a compound of general formula I relative to the total weight of an antimicrobially active compound, in the biocide mixture.

Examples of other antimicrobial compounds which may be used, together with the compound of formula I are quaternary ammonium compounds such as N,N-diethyl-N-dodecyl-N-benzylammonium chloride; N,N-dimethyl-N-octadecyl-N-(dimethylbenzyl)ammonium chloride; N,N-dimethyl-N,N-didecylammonium chloride; N,N-dimethyl-N,N-ethyl-N,N-didodecylammonium chloride; N,N,N-trimethyl-N-didodecylammonium chloride; N,N,N-trimethyl-N-tetradecylammonium chloride; N-benzyl-N,N-dimethyl-N-($C_{12}$–$C_{18}$ alkyl)ammonium chloride; N-(dichlorobenzyl)-N,-N-dimethyl-N-dodecylammonium chloride; N-hexadecylpyridinium chloride; N-hexadecylpyridinium bromide; N-hexadecyl-N,N,N-trimethylammonium bromide; N-dodecylpyridinium chloride; N-dodecylpyridinium bisulphate; N-benzyl-N-dodecyl-N,N-bis(beta-hydroxyethyl)ammonium chloride; N-dodecyl-N-benzyl-N,N-dimethylammonium chloride; N-benzyl-N,N-dimethyl-N-($C_{12}$–$C_{18}$ alkyl) ammonium chloride; N-dodecyl-N,N-dimethyl-N-ethylammonium ethylsulphate; N-dodecyl-N, N-dimethyl-N-(1-naphthylmethyl)ammonium chloride; N-hexadecyl- N,N-dimethyl-N-benzylammonium chloride; N-dodecyl-N,N-dimethyl-N-benzylammonium chloride and 1-(3-chloroallyl)-3,5,7-triaza-1-azonia-adamantane chloride; urea derivatives such as 1,3-bis(hydroxymethyl)-5,5-dimethylhydantoin; bis(hydroxymethyl)urea; 3-(3,4-dichlorophenyl)-1,1-dimethylurea; 3-(4-isopropylphenyl)-1,1-dimethylurea; tetrakis (hydroxymethyl)acetylene diurea; 1-(hydroxymethyl)-5,5-dimethylhydantoin and imidazolidinylurea; amino compounds such as 1,3-bis(2-ethyl-hexyl)-5-methyl-5-aminohexahydro-pyrimidine; hexamethylenetetramine; 1,3-bis(4-aminophenoxy)propane; and 2-[(hydroxymethyl)-amino]ethanol; imidazole derivatives such as 1[2-(2,4-dichloro-phenyl)-2-(2-propenyloxy) ethyl]-1H-imidazole; 2-(methoxycarbonyl-amino)benzimidazole; nitrile compounds such as 2-bromo-2-bromomethylglutaronitrile, 2-chloro-2-chloro-methylglutaro-nitrile; 2,4,5,6-tetra-chloroisophthalodinitrile; thiocyanate derivatives such as methylene(bis)thiocyanate; tin compounds or complexes such as tributyltinoxide, chloride, naphthoate, benzoate or 2-hydroxybenzoate; isothiazolin-3-ones such as 4,5-trimethylene-4-isothiazolin-3-one, 2-methyl-4,5-trimethylene-4-isothiazolin-3-one, 2-methylisothiazolin-3-one, 5-chloro-2-methyl-isothiazolin-3--one, benzisothiazolin-3-one; 2-methylbenzisothiazolin-3-one, 2-octylisothiazolin-3-one, 4,5-dichloro-2-octylisothiazolin-3-one; thiazole derivatives such as 2-(thiocyanomethylthio)-benzthiazole and mercaptobenzthiazole; nitro compounds such as tris(hydroxymethyl)nitromethane; 5-bromo-5-nitro-1,3-dioxane and 2-bromo-2-nitropropane-1,3-diol; iodine compounds such as iodo propynyl butyl carbamate and tri-iodo allyl alcohol; aldehydes and derivatives such as glutaraldehyde (pentanedial), p-chlorophenyl-3-iodopropargyl, formaldehyde and glyoxal; amides such as chloracetamide; N,N-bis(hydroxymethyl)chloracetamide; N-hydroxymethyl-chloracetamide and dithio-2,2-bis(benzmethylamide); guanidine derivatives such as poly (hexamethylenebiguanide) and 1,6-hexamethylene-bis[5-(4-chlorophenyl)biguanide]; thiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine, 6-chloro-2,4-diethyl-amino-s-triazine and 4-cyclopropylamino-2-methylthio-6-t-butylamino-s-triazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and 4-hydroxybenzoic acid and their salts and esters; phenol and derivatives thereof such as 5-chloro-2-(2,4-dichloro-phenoxy)phenol; thio-bis(4-chlorophenol) and 2-phenylphenol; sulphone derivatives such as diiodomethyl-paratolyl sulphone; 2,3,5,6-tetrachloro-4-(methylsulphonyl) pyridine and hexachlorodimethyl sulphone; thioamides such as dimethyldithiocarbamate and its metal complexes, ethylenebisdithiocarbamate and its metal complexes, and 2-mercapto-pyridine-N-oxide and its metal complexes.

Further aspects of the present invention are described in the following illustrative examples in which all preparative details are given in parts by weight unless, otherwise stated. The compounds were evaluated for their antimicrobial properties under sterile conditions using the test protocols described below.

MICROTITRE SCREEN FOR DETERMINING MIC

An overnight culture (18 hours; 37° C.) of the appropriate microorganism was prepared in nutrient broth to give approximately $10^9$ viable cells per 1 ml of culture. 20 ml of the culture was then transferred asceptically to 20 mls of the appropriate medium. 200 ml of this inoculum was then added to all vertical wells of a microtitre plate and 100 ml inoculum added to each subsequent row of vertical wells.

A 5000, ppm solution of the chemical under test was prepared in an appropriate solvent, of which 20 ml was added to the first well of the second row of vertical wells to act as control. The contents of each well were mixed, 100 ml withdrawn and transferred to adjacent horizontal wells in that row. This process was repeated across each vertical row of wells to give a serial dilution of each compound under test ranging from 500 ppm to 0.25 ppm. The microtitre plate was then sealed and incubated at 37° C. for 18 hours. The minimum inhibitory concentration (MIC) was indicated by the well with lowest concentration showing no turbidity.

The nutrient contained Lab-Lemco powder oxoid, Oxoid Bacteriological peptone L34 and sodium chloride in water.

In this particular screen three fungi and two bacteria were used namely *Saccharomyces cerevisiae* (SC), *Aspergillus niger* (AN), *Aternaria alternate* (AA), *Pseudomonas aeruginosa* (PA) and *Staphylococcus aureus* (SA).

EVALUATION AS A PAINT FILM FUNGICIDE

The compounds to be tested were added to samples of a standard laboratory acrylic emulsion paint (based on Revacryl A latex at pH 9) in glass bottles and mixed to given final active ingredient levels in the paint of 1.0, 0.75, 0.5 and 0.3 and 0.1 w/v.

The bottles containing paint plus N-alkyl-BIT were sealed and stored at 40° C. for three days and 4 weeks respectively prior to application.

Two full coats of paint were applied to the upper primed surfaces of beechwood tongue depressors. The lower surfaces of the tongue depressors were protected with two coats of varnish containing no N-alkyl-BIT. The painted surfaces of the depressors were then weathered for 100 hours in an Atlas ES25 Weatherometer set on cam 7 with constant spray. A duplicate set of the painted depressors were not subjected to weathering.

A fungal spore suspension was freshly prepared containing mixed spores of *Alternaria alternata*, *Aurobasidium pullulans*, *Cladosporum herbarum*, *Phoma violacia* and *Stemphylium dendriticum*. A 0.5 ml sample of the spore suspension in sterile deionised water containing 0.05% Aerosol OT was applied to the painted surfaces of the depressors, both weathered and unweathered, by spray inoculation at a concentration of 10E5 spores/mi. The depressors were then incubated at 21° C. in a vermiculate bed chamber for 28 days. The depressors were then examined for fungal growth by both naked eye and by stereomicroscopy (×25).

The evaluation was also carried out using an acrylic paint wherein the pH had initially been adjusted to a value of 10.5.

EXAMPLE 1

Preparation of N-(2-ethylbutyl)benzisothiazolin-3-one

Sodium-BIT (3.46 parts, 0.02M) was dissolved in dimethylformamide (34.6 ml) at 20°–25° C. and 1-bromo-2-ethylbutane (6.6 parts, 0.02M; ex Aldrich) dissolved in dimethylformamide (11.2 ml) added with stirring. The reaction mix was then heated with stirring at 100° C. for 4 hours, and then stirred overnight (14 hrs) at 20°–25° C. Analysis by HPLC showed the reaction to be incomplete, hence further 1-bromo-2-ethylbutane (0.66 parts) was added with potassium carbonate (2 parts) and the reactants heated for a further 4 hrs at 100° C. HPLC analysis revealed virtually no unreacted BIT to be present. The solution was then screened and the dimethylformamide evaporated to give a yellow oil. This oil was diluted with toluene (70 mls) and the toluene solution was washed with dilute aqueous caustic soda followed by water. The toluene solution was then dried over magnesium sulphate, filtered and the toluene evaporated to give a yellow oil.

This oil contained a mixture of N-alkyl and O-alkyl derivatives of BIT which were separated by "flash chromotography". The oil was dissolved in methanol and the oil deposited on a silica support by evaporating the solvent. The coated silica was developed as a column by elating with successive 100 ml aliquots of petroleum ether containing progressively increasing amounts of methylene chloride.

The O-alkyl derivative was eluted in fractions of petroleum ether containing up to 20% by volume methylene chloride. After evaporating the solvents, the O-alkyl derivative was obtained as a colourless oil (Yield=2.6 parts; 55% theory).

The N-alkyl derivative was eluted in fractions of petroleum ether containing over 40% by volume methylene chloride. After evaporating the solvents, the N-alkyl derivative was also obtained as a colourless oil (Yield=1.1 parts; 23% theory). This slowly solidified and was recrystallised from hexane to give colourless crystals (mp 38°–41° C.).

Elemental Analysis theory 66.4% C; 7.2% H; 6.0% N; 13.6% S O—alkyl derivative found 66.0% C; 7.5% H; 5.8% N; 13.0% S N—alkyl derivative found 66.1% C; 7.4% H; 5.8% N; 13.5% S

EXAMPLE 2

Preparation of N-(2-ethylhexyl)benzisothiazolin-3-one 2-chlorosulphenylbenzoyl chloride (10.35 parts; 0.005M) was slowly added to a stirred solution of 2-ethylhexylamine (29.8 parts; 0.23M;) in diethylether (150 ml) at below 5° C. The reactants were then stirred overnight, allowing the temperature to rise to 18° to 20° C. Iced water was then added and the mix made just acid to Congo red by dropwise addition of of concentrated hydrochloric acid, keeping the temperature below 5° C. The ether layer was then separated and dried over magnesium sulphate. The solution was then filtered and the ether evaporated leaving a syrupy oil. This was boiled with petroleum ether (bp 60°–80° C.), the ether layer decanted from some tarry material and then evaporated to dryness leaving a dark yellow oil. This oil was purified by high vacuum distillation in a Kugelrohr and 8.4 parts pale yellow liquid obtained (Yield 64% theory).

Elemental analysis theory:—68.4% C; 8.0% H; 5.3% N; 12.2% S found:—69.3% C; 8.7% H; 5.4% N; 13.0% S

Comparative Examples A to G

The further N-alkyl-BIT were synthesised by the processes described in Example 2 but by replacing the 2-ethylhexylamine used in Example 2 by equivalent amounts of other amines to obtain the BIT listed in Table One below. The N-alkyl-BIT has the structure:

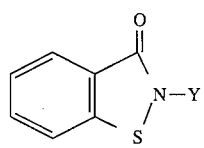

The elemental analysis of the various compounds prepared is listed in Table One.

The MIC of each of these components was determined using the microtitre protocol described hereinbefore. The results are given in Table Two.

TABLE ONE

| | | Method | | Found (%) | | | | Theory (%) | | | |
|---|---|---|---|---|---|---|---|---|---|---|---|
| | Y | a | Yield % | C | H | N | S | C | H | N | S |
| 1 | CH2CH(C2H5)2 | | 23 | 66.1 | 7.4 | 5.8 | 13.5 | 66.4 | 7.2 | 6.0 | 13.6 |
| A | nC6H13 | Ex2 | | 66.3 | 7.6 | 5.1 | | | | | |
| B | cyclohexyl | | | | | | | | | | |
| 2 | CH2CH(C2H5)C4H9n | | 64 | 69.3 | 8.7 | 5.4 | 13.0 | 68.4 | 8.0 | 5.3 | 12.2 |

TABLE ONE-continued

| Y | Method a | Yield % | Found (%) C | H | N | S | Theory (%) C | H | N | S |
|---|---|---|---|---|---|---|---|---|---|---|
| C nC8H17 | Ex2 |  | 68.6 | 8.7 | 4.9 |  |  |  |  |  |
| D CH2CH2Ph | Ex2 | 22.5 | 70.3 | 5.1 | 5.3 | 12.7 | 70.6 | 5.1 | 5.5 | 12.5 |
| E CH(CH3)C6H13n | Ex2 | 54 | 67.6 | 7.8 | 5.4 | 12.2 | 68.4 | 8.0 | 5.3 | 12.2 |
| F CHMe(CH2)3CHMe2 | Ex2 | 54 | 67.7 | 7.8 | 5.2 | 12.6 | 68.4 | 8.0 | 5.3 | 12.2 |
| G CMe2CH2CMe3 | Ex2 | 27 | 68.0 | 7.8 | 5.0 | 12.6 | 68.4 | 8.0 | 5.3 | 12.2 |

Footnote to Table One
(a) indicates the method of preparation.

TABLE TWO

| Ex. or Comp Ex | Y | FUNGI SC | AN | AA | BACTERIA PA | SA |
|---|---|---|---|---|---|---|
| 1 | cls CH2CH(C2H5)2 | <0.25 | 1–2 | 0.8 | 125 | 0.5 |
| A | nC6H13 | <0.25 | 8 | 3 | 62 | 4 |
| B | cyclohexyl | 1 | 16 | 6 | >250 | 32 |
| 2 | CH2CH(C2H5)C4H9n | <0.25 | <0.25 | ND | >250 | <0.25 |
| C | nC8H17 | <0.25 | 16 | ND | >250 | <0.25 |
| D | CH2CH2Ph | 1 | 31 | ND | 125 | <0.25 |
| E | CH(CH3)C6H13n | <0.25 | 8 | ND | >250 | <0.25 |
| F | CHMe(CH2)3CHMe2 | <0.25 | 16 | ND | >250 | <0.25 |
| G | CMe2CH2CMe | 1 | 16 | ND | >250 | <0.25 |

ND No data (or not determined)
SC *Saccharomyces cerevisiae*
AN *Aspergillus niger*
AA *Atternaria alternata*
PA *Pseudomonas aeruginosa*
SA *Staphylococcus aureus*

EXAMPLES 3 AND 4

The compounds of Example 2 and comparative example C were evaluated as paint film fungicides in an acrylic emulsion paint having an initial pH of 9.0 and using the protocol described hereinbefore. The results are given in Table Three which shows that the protection against fungal growth is superior in the case of the N-(β-branched alkyl)-BIT which is Example 2 compared with the linear alkyl analogue which is comparative example C. This is particularly the case after storage of the paint.

TABLE THREE

| Ex-ample | Compound | % AI | No Storage Initial | Weathered | Stored (4 weeks) Initial | Weathered |
|---|---|---|---|---|---|---|
| 3 | C | 10.1 | 5, 5 | 5, 5 | 5, 5 | 5, 5 |
|   |   | 10.3 | 5, 5 | 5, 5 | 5, 5 | 5, 5 |
|   |   | 10.5 | 5, 5 | 5, 5 | 5, 5 | 5, 5 |
|   |   | 10.75 | 4, 5 | 5, 5 | 5, 5 | 5, 5 |
|   |   | 11.0 | 2, 3 | 5, 5 | 3, 4 | 5, 5 |
| 4 | 2 | 10.1 | 5, 5 | 5, 5 | 5, 5 | 5, 5 |
|   |   | 10.3 | 3, 5 | 5, 5 | 4, 4 | 5, 5 |
|   |   | 10.5 | 3, 3 | 5, 5 | 1, 2 | 5, 5 |
|   |   | 10.75 | 2, 2 | 4, 4 | 1, 1 | 4, 4 |
|   |   | 11.0 | 1, 1 | 4, 4 | 0, 1 | 3, 4 |
|   | Control (No Biocide) |   | 5, 5 | 5, 5 | 5, 5 | 5, 5 |

Key
0 = No fungal growth
1 = 1% fungal growth
2 = 1%–10% fungal growth
3 = 10%–30% fungal growth
4 = 30%–70% fungal growth
5 = >70% fungal growth

EXAMPLES 5 TO 8

Several N-alkyl-BIT were evaluated as paint film fungicides in an acrylic emulsion paint having an initial pH of 10.5 using the protocol as described hereinbefore. The results are given in Table Four and shows that the N-(B-branched alkyl)-BIT of Example 6 is significantly better than the N-(loweralkyl)-BIT of Example 5. Example 6 is significantly better both before and after weathering compared with Example 8 which is an important commercial fungicide, and is superior to Example 7 after weathering which is a market leading paint-film fungicide.

TABLE FOUR

| Example | Com-pound | % AI | No Storage Unweat-hered | Weat-hered | Stored (4 weeks) Unweat-hered | Weat-hered |
|---|---|---|---|---|---|---|
| 5 | A | 0.1 | 0 0 | 3 4 | 1 2 | 5 5 |
|   |   | 0.3 | 0 0 | 1 2 | 0 1 | 3 4 |
|   |   | 0.5 | 0 0 | 0 1 | 0 0 | 0 1 |

TABLE FOUR-continued

| Example | Compound AI | % | No Storage Unweathered | | Weathered | | Stored (4 weeks) Unweathered | | Weathered | |
|---|---|---|---|---|---|---|---|---|---|---|
| | | 0.75 | 0 | 0 | 0 | 0 | 0 | 0 | 0 | 0 |
| | | 1.0 | 0 | 0 | 0 | 0 | 0 | 0 | 0 | 0 |
| 6 | 1 | 0.1 | 0 | 0 | 2 | 3 | 0 | 1 | 4 | 5 |
| | | 0.3 | 0 | 0 | 0 | 1 | 0 | 0 | 0 | 1 |
| | | 0.5 | 0 | 0 | 0 | 0 | 0 | 0 | 0 | 1 |
| | | 0.75 | 0 | 0 | 0 | 0 | 0 | 0 | 0 | 0 |
| | | 1.0 | 0 | 0 | 0 | 0 | 0 | 0 | 0 | 0 |
| 7 | T | 0.1 | 0 | 0 | 0 | 1 | 0 | 1 | 4 | 5 |
| | | 0.3 | 0 | 0 | 0 | 0 | 0 | 0 | 2 | 3 |
| | | 0.5 | 0 | 0 | 0 | 0 | 0 | 0 | 0 | 1 |
| | | 0.75 | 0 | 0 | 0 | 0 | 0 | 0 | 0 | 0 |
| | | 1.0 | 0 | 0 | 0 | 0 | 0 | 0 | 0 | 0 |
| 8 | SK | 0.1 | 0 | 0 | 4 | 5 | 5 | 5 | 5 | 5 |
| | | 0.3 | 0 | 0 | 1 | 2 | 4 | 4 | 5 | 5 |
| | | 0.5 | 0 | 0 | 0 | 0 | 0 | 1 | 4 | 5 |
| | | 0.75 | 0 | 0 | 0 | 1 | 0 | 0 | 3 | 3 |
| | | 1.0 | 0 | 0 | 0 | 0 | 0 | 0 | 0 | 1 |
| Control No biocide | | | 5 | 5 | 5 | 5 | 5 | 5 | 5 | 5 |

Key
0 = No fungal overgrowth
1 = <1% fungal overgrowth
2 = 1%–10% fungal overgrowth
3 = 10%–30% fungal overgrowth
4 = 30%–70% fungal overgrowth
5 = >70% fungal overgrowth
T is 3-iodo-2-propynylbutylcarbamate
SK is N-octyl (n)-isothiazolin-3-one

EXAMPLE 9

Preparation of N-cyclohexylmethyl benzisothiazolinone
This was made by the method described in J.Org.chem 1954, 19, 103.

a) Preperation of 2,2'-dithio-N,N'-bis(2-cyclohexyl)dibenzamide

Dithiodibenzoyl chloride (3.43 parts, 0.01M) was added in portions to a stirred solution of aminomethylcyclohexane (2.26 parts, 0.02M; ex Aldrich) and triethylamine (2.02 parts; 0.02M; ex Aldrich) in diethylether (50 ml) at at 0° to 5° C. The reaction mix was stirred overnight, allowing to warm to 20° to 25° C. when a thick precipitate of the diamide formed. Most of the ether was removed by evaporation and the residue was stirred with methylated spirits (50 ml), water (40 ml) and concentrated hydrochloric acid until just acid to Congo Red. The bisamide was then filtered and recrystallised from n-propanol. The bisamide was obtained as a white crystalline solid (4.7 parts—95% theory) mp 219°–221° C.

Elemental analysis: Theory 64.9%C; 7.2%H; 6.3%N; 14.4%S Found 65.1%C; 7.3%H; 6.3%N; 12.8%S b) Preparation of Title Compound
The bisamide from above (2.12 parts; 0.00845M) was dissolved in pyridine (25 ml) and stirred at 20° to 25° C. whilst a solution of iodine (2.14 parts; 0.00843M) in pyridine (15 ml) was added dropwise. Initially, the iodine solution was rapidly decolourised. After addition of all the iodine, the reaction mix was stirred for a further 30 minutes and then evaporated to dryness. The product (3.3 parts; 73% theory) was obtained as an oil which was recrystallised from toluene to give almost colourless crystals (2.9 parts) mp 70°–72° C.

Elemental analysis: Theory 68.0%C; 6.9%H; 5.7%N; 13.0%S Found 68.6%C; 7.0%H; 5.8%N; 12.2%S

EXAMPLE 10

Preparation of 6-chloro-2(2-ethylhexyl)benzothiazole
This was prepared in analogous manner to the method described in Example 9 but replacing the bis acid chloride with 4,4'-dichloro dithiodibenzoyl chloride (1.3 parts; 0.00315M) and replacing the aminomethyl cyclohexane with an equivalent amount of 2-ethylhexylamine (0.815 parts; 0.0063M) and using less triethylamine (0.635 parts; 0.0063M).

The bisamide obtained was recrystallised from aqueous methanol to give a white crystaline solid (1.7 parts; 86% theory) mp 188°–90° C.

Elemental analysis: Theory 60.3%C; 7.0%H; 4.7%N; 10.7%S Found 60.0%C; 7.2%H; 4.8%N; 11.1%S The bisamide from above (1.6 parts; 0.00268M) was converted into the isothiazolinone using iodine (0.68 parts; 0.00268M) in a similar process to that described in Example 9(b). The product was recrystallised from petroleum ether to give a white crystalline solid (0.9% parts; 56% theory) mp 64°–66° C.

Elemental analysis: Theory 60.5%C; 6.7%H; 4.7%N; 10.8%S Found 60.7%C; 6.8%H; 4.7%N; 10.9%S

EXAMPLES 11 AND 12

The Minimum Inhibitory Concentrations of the two isothiazolinones whose preparation is described in Examples 9 and 10 were determined using the Microtitre Screen described hereinbefore. The results are given in Table Five below.

TABLE FIVE

| EXAMPLE | COMPOUND | MIC (PPM) | | | |
|---|---|---|---|---|---|
| | | SC | An | Aa | Sa |
| 11 | Ex 9 | 0.4 | 12 | 3 | 0.8 |
| 12 | Ex 10 | 0.8 | 12 | 12 | <0.05 |

I claim:
1. A compound of formula I

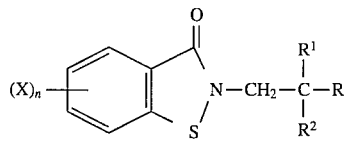

and salts thereof wherein
R and $R^1$ are alkyl or substituted alkyl containing at least 2 carbon atoms;
$R^2$ is hydrogen, alkyl or substituted alkyl; or
R and $R^1$ together with the carbon atom to which they are attached complete an alicyclic ring;
X is halogen, $C_{1-4}$-lower alkyl, $C_{1-4}$-lower alkoxy, nitro, nitrile, hydroxy, carboxy, or alkoxycarbonyl, and
n is 0 to 4, the total number of carbon atoms represented by R, $R^1$ and $R^2$ when not hydrogen being less than 18.

2. A compound as claimed in claim 1 wherein the substituent in alkyl is selected from phenyl, cyclohexyl, halogen, nitro, nitrile, hydroxy, carboxy, alkoxycarbonyl, acyloxy or $C_{1-4}$-lower alkoxy.

3. A compound as claimed in claim 1 wherein $R^2$ is hydrogen and R and $R^1$ are each alkyl.

4. A compound as claimed in claim 1 wherein n is 0.

5. The compounds N-(2-ethylhexyl)-benzisothiazolin-3-one and N-(2-ethylbutyl)-benzisothiazolin-3-one.

6. A composition comprising a carrier and a compound of formula

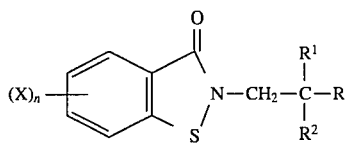

wherein

R and $R^1$ are alkyl or substituted alkyl containing at least 2 carbon atoms;

$R^2$ is hydrogen, alkyl or substituted alkyl; or

R and $R^1$ together with the carbon atom to which they are attached complete an alicyclic ring;

X is halogen, $C_{1-4}$-lower alkyl, $C_{1-4}$-lower alkoxy, nitro, nitrile, hydroxy, carboxy or alkoxycarbonyl; and n is 0 to 4, the total number of carbon atoms represented by R, $R^1$ and $R^2$ when not hydrogen being less than 18.

7. A method for inhibiting the growth of micro-organisms on, or in a medium which comprises treating the medium with a compound as claimed in claim 1.

8. A method a claimed in claim 7 wherein the medium is a paint or latex.

* * * * *